United States Patent [19]
Zimmermann et al.

[11] Patent Number: 5,217,884
[45] Date of Patent: Jun. 8, 1993

[54] HYDROXYLATION OF METHYL GROUPS IN AROMATIC HETEROCYCLES BY MICROORGANISMS

[75] Inventors: Thomas Zimmermann, Naters; Andreas Kiener, Visp; Shigeaki Harayama, Les Avanchets, all of Switzerland

[73] Assignee: Lonza Ltd., Gampel, Switzerland

[21] Appl. No.: 764,176

[22] Filed: Sep. 23, 1991

[30] Foreign Application Priority Data

Sep. 24, 1990 [CH] Switzerland ............ 3066/90

[51] Int. Cl.$^5$ .................. C12P 7/22; C12P 17/00; C12P 17/12; C12P 17/14
[52] U.S. Cl. ................... 435/117; 435/156; 435/122; 435/120; 435/121; 435/126
[58] Field of Search ............. 435/117, 126, 155, 156, 435/121, 252.33, 252.34, 320.1, 120, 122; 536/27

[56] References Cited

FOREIGN PATENT DOCUMENTS 0277674 8/1988 European Pat. Off. .

OTHER PUBLICATIONS

Harayama et al., J. Bacteriol., 171, (1989), pp. 5048–5055.
Hansen et al., J. Bacteriol., 135, (1978), pp. 227–238.
Humphreys et al., Biochim., Biophys. Acta, 383, (1975), pp. 457–463.
Current Protocols in Molecular Biology, John Wiley & Sons, N.Y., (1987), Section 2.6.
Current Protocols in Molecular Biology, John Wiley & Sons, N.Y., (1989), Section 3.16.
Lederberg et al., J. Bacteriol., 119, (1974), pp. 1072–1074.
Zimmermann et al., Molecular Microbiology, 5, (1991), pp. 1483–1490.
O'Connor et al., J. Bacteriol., 169, (1987), pp. 4457–4462.
Itoh et al., Gene, 36, (1985), pp. 27–36.
Bagdasarian et al., Gene, 26 (1983), pp. 273–282.
Furste et al., Gene, 48, (1986), pp. 119–131.
Bolivar et al., Gene, 2, (1977), pp. 95 to 113.
Kado et al., J. Bacteriol., 145, (1971), pp. 1365 to 1373.
Keil et al. (Feb. 1987), J. Bacteriol., vol. 169(2), pp. 764–770.

Primary Examiner—Richard A. Schwartz
Assistant Examiner—Philip W. Carter
Attorney, Agent, or Firm—Fisher, Christen & Sabol

[57] ABSTRACT

A process using microorganisms which contain genes, which form an active xylene monooxygenase, which form no effective, chromosomally or plasmid-coded alcohol hydrogenase, and which are, thus, capable of hydroxylating methyl groups on aromatic 5- or 6-atom heterocycles to the corresponding hydroxymethyl derivatives, for the production of hydroxymethylated 5- or 6-atom heterocycles.

17 Claims, 1 Drawing Sheet

HYDROXYLATION OF METHYL GROUPS IN AROMATIC HETEROCYCLES BY MICROORGANISMS

BACKGROUND OF THE INVENTION

1. Field Of The Invention

The invention relates to a new microbiological process for hydroxylating methyl groups in aromatic 5- or 6-atom heterocycles as well as to new hybrid plasmids and new production strains especially suited for the process.

2. Prior Art

A microbiological process for the terminal hydroxylation of aliphatic side chains by genetically changed microorganisms is known from European Published Patent Application No. 0277674. This reaction is catalyzed by the alkane hydroxylase, coded by genes alkBA from the OCT-plasmid of Pseudomonas oleovorans. These microorganisms were changed genetically so that they are no longer capable of further oxidizing the resulting hydroxyl groups to the acid. But the natural expression and regulation (alkR) of these genes were maintained. These microorganisms have no activity for the oxidation of methyl groups in heterocycles, but catalyze only the hydroxylation of alkanes and alkylated compounds with alkyl radicals with 6 to 12 carbon atoms.

Further, it is known from Harayama et al., J. Bacteriol. 171, (1989), pages 5048 to 5055, that microorganisms of the species Pseudomonas putida with plasmid pWWO can oxidize the methyl group on toluene in three steps to benzoic acid. By the action of xylene monooxygenase (xylMA), benzyl alcohol first results, which in two further steps is then catalyzed by an alcohol dehydrogenase (xylB) and converted by an aldehyde dehydrogenase (xylC) to the acid. Both the xyl genes, which code for the enzymes of the xylene catabolism, and the genes which are responsible for the regulation of the xyl genes on plasmid pWWO, are in this strain. Thus, the properties, the identification, the cloning, the selection and the restriction map of the genes xylMABCN responsible for the oxidation of the methyl group are known from it. The function of gene xylN is still unknown. But no microbiological process is known which can hydroxylate methyl groups in aromatic 5- or 6-atom heterocycles. Moreover, those specifically hydroxymethylated heterocycles are chemically difficult to obtain.

BROAD DESCRIPTION OF THE INVENTION

The main object of the invention is to provide a microbiological process for specific hydroxylation of methyl groups in aromatic 5- or 6-atom heterocycles to the correspondingly pure hydroxymethylated derivatives, and the products must not be further catabolized. Other objects and advantages of the invention are set out herein or are obvious herefrom to one skilled in the art.

The objects and advantages of the invention are achieved by the process, hybrid plasmids and production strains of the invention.

The invention involves a microbiological process of hydroxylating the methyl group or groups in a 5- and 6-atom aromatic heterocycle. The invention process is performed with microorganisms, which:

(a) contain the genes of a Pseudomonas TOL plasmid, which form an active xylene monooxygenase, and
(b) form no effective chromosomally or plasmid coded alcohol dehydrogenase, and thus, are capable of hydroxylating methyl groups of aromatic 5- or 6-atom heterocycles to the corresponding hydroxymethyl derivative, and the heterocycle is used as substrate for the reaction and exhibits no substituents on the carbon atom adjacent to the methyl group to be hydroxylated and the hydroxymethyl derivative is not further catabolized.

The hydroxymethylated heterocycles produced by the invention process are, for example, important intermediate products for the production of pharmaceutical agents and agricultural chemicals.

BRIEF DESCRIPTION OF THE DRAWING

In the drawing:

The FIGURE is a restriction map of the genes for forming a xylene monooxygenase of Pseudomonas TOL plasmid pWWO, in the microorganisms used in the invention process.

DETAILED DESCRIPTION OF THE INVENTION

Figure 1:
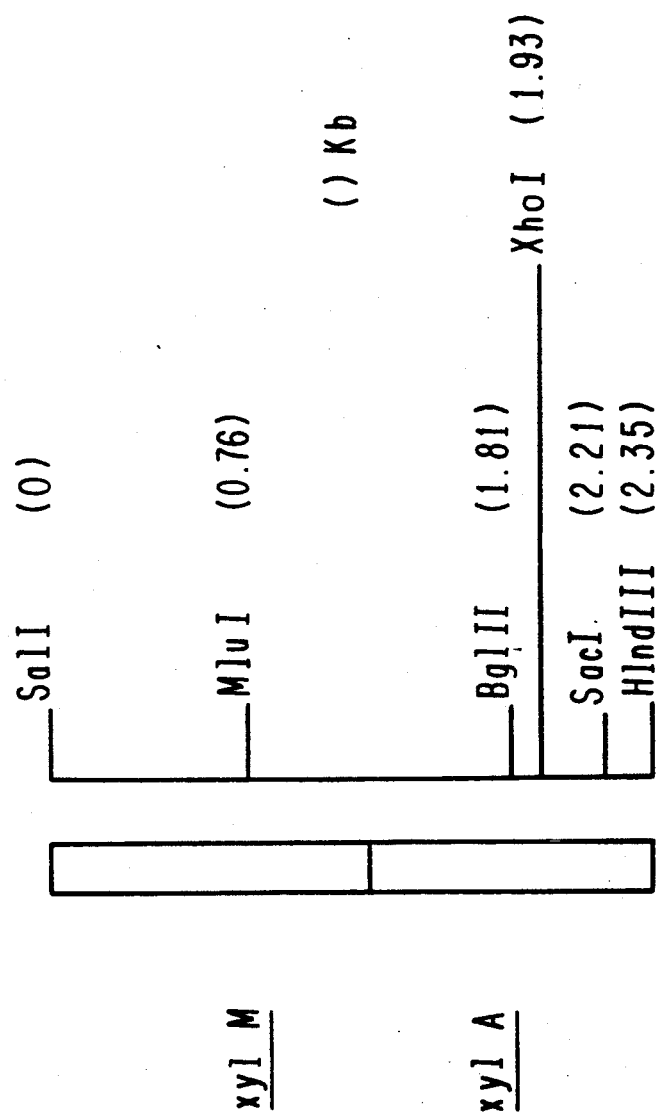

The microorganisms used in the invention process suitably contain the genes for forming a xylene monooxygenase of Pseudomonas TOL plasmid pWWO of the FIGURE, which are characterized by the following restriction map, and have already been described in J. Bacteriol., 171, (1989), pages 5048 to 5055:

Source of the xylene monooxygenase genes

As a source for the xylene monooxygenase genes, Pseudomonas putida can be used with the TOL plasmid pWWO, which, e.g., can be obtained under ATCC 33015 in the American Type Culture Collection.

The genetic data, which is the code for the xylene monooxygenase, can then thus be obtained by (a) the TOL plasmid DNA being isolated from this microorganism, which is used as a source for the DNA, then (b) this TOL plasmid DNA being digested to isolate the gene for the xylene monooxygenase and the specific gene sequence, then (c) being introduced in an expression vector, and as a result, (d) a hybrid plasmid resulting. This hybrid plasmid can then be introduced in a microorganism (e) (host strain), suitable for the process, by transformation (f). This transformed host strain then forms production strain (g) [after selection (h)] for fermentation process (i) according to the invention.

(a) Isolation of the TOL plasmid DNA

The TOL plasmid DNA can be obtained according to methods usual and known to one skilled in the art, such as, according to the method of Hansen and Olsen [J. Bacteriol., 135, (1978), pages 227 to 238] or Humphreys et al. [Biochim. Biophys. Acta, 383, (1975), pages 457 to 463]. The method of Humphreys et al. [Biochim. Biophys. Acta, 383, (1975), pages 457–463] is suitably used for the isolation of large amounts of TOL plasmid DNA, by Pseudomonas putida (ATCC 33015) being completely lysed and then the TOL plasmid being isolated by density gradient centrifuging.

(b) Cleavage with restriction enzymes and isolation of DNA by agarose gel electrophoresis.

After isolation of the TOL plasmid DNA, the TOL plasmid DNA is suitably cleaved with restriction enzymes SalI and HindIII, and then the DNA section, which is the code for the xylene monooxygenase, can be isolated by agarose gel electrophoresis, according to Current Protocols in Molecular Biology, John Wiley and Sons, New York, 1987), section 2.6, "Isolation and Purification of Large DNA-Restriction Fragments from Agarose Gels."

This DNA section is characterized, as already described before, by the following restriction map of the FIGURE and contains no genes which are coded for an effective alcohol dehydrogenase:

(c) Ligation of the DNA section in expression vectors

The thus-obtained gene section can be ligated to a hybrid plasmid by the usual and known molecular biological techniques with a previously equally cut expression vector DNA. Expression vectors usually contain a suitable, mostly adjustable promoter. One or more singular cutting sites for restriction enzymes advantageously lie behind this promoter in the transcription direction. Then, the desired gene section, in whose expression there is interest, is usually inserted in these cutting sites.

Listed in Table 1 are suitable expression vectors. For the process according to the invention, expression vectors with a broad host range, such as, pME285, pKT240, pMMB67EH or pMMB67EH*, are suitably used.

These expression vectors with restriction enzymes SalI and HindIII are suitably cut, and the resulting restriction ends with the isolated TOL plasmid DNA are then ligated by, for example, T4 DNA ligase. Also, optionally, other methods for ligation can be used, such as, those which are described in Current Protocols in Molecular Biology, John Wiley and Sons, New York, (1989), section 3.16,"Subcloning Of DNA Fragments".

(d) Hybrid plasmids

Hybrid plasmids pL03, pL04 and pL05, suitably thus resulting, are also a component of the invention, exhibit a broad host range and can consequently be used in host strains with high substrate and feedstock tolerance. These hybrid plasmids are suitably decoupled from the natural regulation system. Consequently, hybrid plasmid pL04 (consisting of expression vector pMMB67EH and the TOL plasmid gene) is characterized by the above-described restriction map with promoter $P_{tac}$ controlled by repressor gene lacIo. The expression of the TOL plasmid genes can consequently be induced with isopropyl thiogalactoside (IPTG).

The expression of the TOL plasmid genes in hybrid plasmid pL05 [consisting of expression vector pMMB67EH* and the TOL plasmid gene characterized by the restriction map set out above and noted as previously being described in J. Bacteriol., 171, (1989), pages 5048 to 5055], with promoter $P_{tac}$, is permanently (constitutively) induced because of the missing repressor gene lacIg.

Repressor gene lacIg in pMMB67EH* is suitably mutated for this purpose by introducing a kanamycin resistance. It is also possible to use a hybrid plasmid with a narrow host range. Suitably pGSH2836 with promoter lambda $P_L$ is used as a hybrid plasmid with a narrower host range, and the expression of the TOL plasmid genes is permanently (constitutively) induced. If, for example, Escherichia coli (E. coli) K12* is used as a host for pGSH2836, repressor gene cI857, integrated chromosomally there, has to be deactivated by temperature to achieve an expression of promoter lambda $P_L$.

Hybrid plasmid pGSH2836 is deposited in E. coli K12* under deposit number DSM 6154 in the German Collection for Microorganisms and Cell Cultures GmbH, Mascheroderweg 1b, D-3300 Braunschweig. Hybrid plasmids pL04 and pL05 are deposited in E. coli K12* (pL04) or in Pseudomonas putida (pL05), as described in the following sections.

(e) Host strains

Because of the broad host range, hybrid plasmids (pL03, pL04, pL05) thus resulting can be introduced in a multiplicity of host strains. Host strains with high substrate and feedstock tolerance are suitably used, such as, those of genus Pseudomonas, Acinetobacter, Rhizobium, Aorobacterium or Escherichia.

(f) Transformation

The introduction of the hybrid plasmids in the above-described host strains can take place according to the usual and known methods, preferably according to the method of Lederberg and Cohen [J. Bacteriol., 119, (1974), pages 1072 to 1074].

(g) Production strains

As production strains, all of those listed in Table 2 are suitably used. The microorganisms transformed with hybrid plasmids pL03, pL04 and pL05 (Table 2) are new and, thus, also a component of the invention.

Microorganism E. coli K12* is preferably used, transformed with hybrid plasmid pL04, deposited on Aug. 29, 1990, under deposit number DSM 6153, or microorganism Pseudomonas putida JD7 is used, transformed with hybrid plasmid pL05, deposited on Aug. 29, 1990, under deposit number DSM 6152, as well as their descendants and mutants. The two deposits took place at the German Collection of Microorganisms and Cell Cultures GnbH, Mascheroderweg 1b, D-3300 Braunschweig.

Also, these microorganisms can be used as production strains which contain a natural TOL plasmid and in which then, the gene, which is the code for an effective alcohol dehydrogenase, is removed or deactivated. The deactivation or removal can take place by standard mutation, e.g., with acridine orange by a transposon insertion or by the method below of "gene replacement" with homologous recombination [A. Zimmermann et al., Molecular Microbiology, 5, (1991), pages 1483 to 1490].

In these production strains, the expression of the TOL plasmid genes takes place, for example, by induction with compounds such as toluene, xylene or cymene.

The removal of the alcohol dehydrogenase gene suitably takes place so that a previously produced auxiliary hybrid plasmid, in which the alcohol dehydrogenase gene is already removed, is taken up by homologous recombination in the natural TOL plasmid ("gene replacement" with homologous recombination). Then, the alcohol dehydrogenase is suitably removed in the natural TOL plasmid by this taking up.

(h) Selection of the transformed microorganisms (production strains)

The transformants can usually be selected on a minimum medium glucose agar with corresponding inhibition concentration of suitable antibiotics. The antibiotic-resistant markers used are listed in Table 1.

(i) Fermentation process

According to the invention, the production strains obtained according to the above-described processes, as well as their descendants and mutants, are used for the process according to the invention for hydroxylating methyl groups in aromatic 5- or 6- atom heterocycles.

As substrates for the reaction, methylated aromatic 5- or 6-atom heterocycles can be used which contain one or more heteroatoms from the series oxygen, nitrogen and sulfur. Suitable 5-atom heterocycles are, for example, methylated thiophene, methylated furan, methylated pyrrole, methylated thiazole, methylated pyrazole and methylated imidazole derivatives, all of which have no substituents on the carbon atom adjacent to the methyl group to be hydroxylated. Preferably, 3,5-dimethylpyrazole, 4-methylthiazole and 2,5-dimethyl-thiophene are used as the 5-atom heterocycles.

Suitable 6-atom heterocycles are, for example, methylated pyridine, methylated pyrimidine, methylated pyrazine and methylated pyridazine derivatives, which have no substituents on the adjacent carbon atom to the methyl group to be hydroxylated. Preferably, 2-chloro-5-methylpyridine, 2,5-dimethylpyrazine and 2,6-dimethylpyrimidine are used as the 6-atom heterocycles.

Before the addition of the substrate, the cells are cultured up to an optical density at 650 nm ($OD_{650}$) of 1 to 200 in the culture medium, preferably up to an optical density of 5 to 100.

The reaction can take place either under the single or continuous addition of the substrate, so that the substrate concentration in the culture medium does not exceed 20 percent (w/v) or (v/v) for liquid substrates. Preferably, the addition of the substrate takes place so that the substrate concentration in the culture medium does not exceed 5 percent (w/v) or (v/v).

The reaction is usually performed with resting cells in a pH range of 4 to 11, preferably 6 to 10. The reaction is usually performed at a temperature of 15° to 50° C., preferably at a temperature of 25° to 45° C.

After the reaction, the corresponding hydroxymethyl derivative can be isolated in the known manner.

EXAMPLE 1

Cloning of Genes xylMA 1.1. Plasmid preparation

[Humphreys et al., Biochim. Biophys. Acta, 383 (1975), pages 457 to 483].

The cells of 1 1 of a fully grown bacteria culture, Pseudomonas putida pWWO (ATCC 33015), were centrifuged out. After resuspension of the cells in 10 ml of 25 percent saccharose in 0.05 mol of tris buffer, pH 8.0, .5 ml of lysozyme solution (20 mg/ml in 0.25 mol of tris buffer, pH 8.0) was added. Then, the mixture was incubated for 5 minutes on ice; 10 ml of 0.25 mol of $Na_2$ EDTA (pH 8) was added and it was further incubated for 5 minutes on ice. Then, 15 ml of Brij® polyoxyethylene lauryl ether/DCL solution (1 percent of Brij® 58, 0.4 percent of sodium deoxycholate in 0.01 mol of tris buffer, 0.001 mol of $Na_2$ EDTA; pH 8.0) was added. Good, uniform, thorough mixing followed, then there was incubation on ice for 30 minutes until complete cell lysis.

After centrifuging for 45 minutes at 4° C. at 16,000 rpm, the supernatant was decanted in an autoclaved measuring cylinder. 3 percent (w/v) of NaCl and of 10 percent PEG (polyethylene glycol) was added. By careful turning of the cylinder, which was closed with parafilm, a solution was produced. It was incubated for 2 hours at 4° C. and then centrifuged for 2 minutes at 5,000 rpm. Then, the supernatant was decanted and the precipitate was dissolved in 5 ml of TES- buffer (0.05 mol of TRIS, 0.005 mol of $Na_2$ EDTA, 0.05 mol of NaCl, pH 8.0); this was followed by conversion in autoclaved 15 ml Corex test tubes with 8.0 g of calcium chloride. After adding 0.6 ml of ethidium bromide solution (10 mg/ml), it was incubated for 30 minutes on ice.

After centrifuging for 30 minutes at 4° C. at 12,000 rpm, it was carefully decanted to remove the precipitated PEG from the solution. After ultracentrifuging of the solution in closed test tubes with a 50TI-rotor at 40,000 rpm for 30 hours at 18° C., the plasmid band was isolated from the $CsCl_2$ gradients with a cannula in front of the UV transilluminator.

The ethidium bromide was removed from the plasmid preparation by shaking out with n-butanol. Next, isopropanol precipitation of the plasmid DNA and drying of the precipitate in a Speed VaC® concentrator was followed by resuspension of the plasmid preparation in 0.01 mol of tris buffer (0.001 mol of $Na_2$ EDTA, pH 8.0).

1.2 Isolation of DNA fragments xylMA from agarose gels

The plasmid DNA cut with SalI and HindIII (4 units each per microgram of plasmid DNA) was subjected to a preparative agarose gel electrophoresis (0.6 percent (w/v) agarose in TBE buffer [0.09 mol of tris-borate, 2.5 mmol of $Na_2$ EDTA, pH 8.3, ethidium bromide (100 micrograms/100 ml)].

A DEAE cellulose membrane cut into small strips was prepared in water and inserted in slots in the agarose gel directly in front of the desired DNA fragment band. DNA was allowed to accumulate in the voltage field on the membrane. Optionally, higher DNA bands were retained with additional membranes. The accumulated DNA was washed off from the membrane with 500 microliters of elution buffer (20 mmol of TRIS, pH 7.5, 1 mmol of $Na_2$ EDTA, 1.5 mol of NaCl) for 1 hour at 65° C.

The membrane was removed and washed off. Ethidium bromide was extracted with $H_2O$-saturated n-butanol from the DNA solution. The DNA was precipitated with isopropanol. The precipitate was dried in a Speed VaC® concentrator, followed by resuspension of the fragment preparation in 0.01 mol of tris buffer, 0.001 mol of $Na_2$ EDTA, pH 8.0.

1.3 Ligation of DNA fragments xylMA with expression vectors

[Current Protocols in Molecular Biology, John Wiley and Sons, New York, (1989), section 3.16, Subcloning Of DNA Fragments]

(a) Preparation of hybrid plasmid poL04
Preparation of the expression vector DNA Before the ligation, the pMMB67EH vector DNA (2 micrograms) was cut with 10 units each of SalI and HindIII in the corresponding ligation buffer [20 mmol of tris buffer, 10 mmol of DTT (dithioerythritol), 10 mmol of $MgCl_2$ and 0.6 mmol of ATP; pH 7.2]. This cut DNA was then dephosphorylated with 4.8 units of alkaline phosphatase. The DNA was precipitated and washed repeatedly with isopropanol.

Ligation of the xylMA-DNA with the expression vector-DNA

For the ligation, the respective DNA samples (in various quantitative ratios in excess of the insert-DNA) were added together, subjected to an isopropanol precipitation, and the dried precipitates were taken up in 40 to 100 microliters of ligation buffer (20 mmol of tris buffer, 10 mmol of DTT, 10 mmol of $MgCl_2$ and 0.6 mmol of ATP, pH 7.2). The ligation took place after adding 0.2 units of T4-DNA ligase per microgram of DNA overnight with incubation at 12° to 16° C. Then, the ligation mixture was used directly for transformation.

(b) Preparation of hybrid plasmid pL05

Analogously to Example 1.3 (a), expression vector pMMB67EH* was prepared and according to Example 1.3 (a), the xylMA genes were then ligated in this vector.

1.4 Transformation of competent cells with hybrid plasmid DNA (pL04)

a) Concentration of hybrid plasma DNA (pL04)

The cells of a 25 ml culture of *E. coli* S17-1 were harvested as an auxiliary strain at an $OD_{546}=2.0$ and were made competent according to the method of Lederberg and Cohen [J. Bacteriol., 119, (1974), 1072 to 1074]. After washing these cells in 10 ml of 0.1 mol of $MgCl_2$, the cells were incubated for 30 minutes in 10 ml of 0.1 $CaCl_2$ on ice. These cells in 1 ml of 0.1 mol of $CaCl_2$ were centrifuged and resuspended. 0.2 ml each of the cell suspension was mixed with 0.5 microgram of ligated hybrid plasmid DNA for transformation. The suspension was incubated for more than 30 minutes on ice, that is, 2-minute thermal shock at 42° C.

Then, the respective cell suspensions were filled up to 5 ml with preheated nutrient yeast broth (Oxoid, Wesel, FRG), and incubated for 1 hour without shaking and another hour with shaking for the expression of the genes at optimum growth temperature of the recipient cells (*E. coli* 517-1). Aliquots of the transformed cultures were placed on corresponding selective media (nutrient agar, 100 micrograms of ampicillin per ml).

(b) Transformation of pL04 in the production strain

Hybrid plasmid pL04 was isolated from the *E. coli* S17-1-strain with pL04 corresponding to Examples 1.1 and 1.2. Then, *E. Coli* K12* was transformed according to the method in Example 1.4 (a) with hybrid plasmid pL04. The selection took place in accordance with the selective medium (nutrient agar, 100 micrograms of ampicillin per ml).

1.5 Transformation of competent cells with hybrid plasmid pL05

Corresponding to Example 1.4, hybrid plasmid pL05 was transformed into *Pseudomonas putida* JD7. The selection took place with selective medium (nutrient agar, 50 micrograms of kanamycin per ml).

EXAMPLES 2 TO 8

Hybrid plasmid pL03 was produced corresponding to Example 1.3.

Hybrid plasmids pGSH2836, pL03, pL04 and pL05 in host strains *E. coli* K12*, *Pseudomonas aeruginosa* PA025, *Pseudomonas putida* JD7 and *Pseudomonas putida* were transformed corresponding to Examples 1.4 and 1.5.

The reaction rates of these production strains are compiled in Table 2.

EXAMPLE 9

Construction of the xylB mutants 9.1 Construction of plasmid pL010

Genes xylMABCN were isolated from plasmid pGSH2816 [Harayama et al., J. Bacteriol., 171, (1989)] by EcoRI and HpaI restriction and then ligated in the equally cut vector pBR322 [Bolivar et al., Gene, 2, (1977), p. 95 ff].

9.1.1 Cleavage with restriction enzymes and isolation of the DNA by agarose gel electrophoresis The pGSH2816-DNA cut with EcoRI and HpaI (5 units each per microgram of DNA) was separated by preparative agarose gel electrophoresis (0.7 percent agarose in 0.09 mol of tris-borate, and 2.5 mmol of Na-EDTA; pH 8.3), and the DNA fragments of the required size were isolated (corresponding to Example 1.2).

9.1.2 Ligation of the DNA fragment with xylMABCN in pBR322

[Current Protocols in Molecular Biology, John Wiley and Sons, New York, (1988), Section 3.16, Subcloning Of DNA Fragments]

(a) Preparation of the vector-DNA

The pBR322-DNA (2 micrograms) with 10 units each of EcoRI and ScaI in the restriction buffer (50 mmol of TRIS, 10 mmol of $MgCl_2$, and 100 mmol of preparative agarose gel electrophoresis) was separated before the ligation. The desired 3850 bp band was isolated as described in Example 9.1.1.

(b) Ligation

For the ligation, the respective DNA samples (in various quantitative ratios in excess of the insert-DNA) were added together, mixed with ligation buffer (20 mmol of TRIS, 10 mol of DTT, 10 mmol of $MgCl_2$ and 0.6 mmol of ATP, pH 7.2) and incubated overnight at 12° to 16° C. after adding 1 unit of T4 DNA ligase. Then, the ligation mixture was used directly for transformation.

(c) Transformation of *E. coli* C600

[According to Example 1.4.]

The selection took place on nutrient agar with tetracycline (25 micrograms/microliter). According to restriction control, sizable amounts of pLOIO-DNA were purified by CsCl gradient.

9.2 Design of plasmid pL011

9.2.1 Cleavage of pL101 DNA with restriction enzymes 5 micrograms of pL010 DNA was cut with 22 units of HindIII in the restriction buffer (10 mmol of TRIS, 10 mmol of $MgCl_2$, 50 mmol of NaCl and 1 mmol of DTT, pH 7.5) and subjected to a preparative agarose gel electrophoresis. Two fragments with sizes of 3.8 kb and 2.9 kb were isolated as described in Example 9.1.1 and taken up in 45 and 30 microliters of water, respectively. They contained vector pBR322 and the range of xyl genes except for xylB.

9.2.2 Ligation

Both fragments isolated in Example 9.2.1 were used for ligation, as described in Example 9.1.2b. For this purpose, 45 microliters of fragment 3.8 kb, 30 microliters of fragment 2.8 kb, 10 microliters of ligation buffer, 10 microliters of 10 mmol of ATP and 1 microliter of T4 DNA ligase were mixed and incubated overnight at 12° to 16° C. Then, the DNA was precipitated with ethanol and taken up in 10 microliters of water.

9.2.3 Transformation of *E. coli* HB101

The DNA obtained according to Example 9.2.2 was used directly for transformation of *E. coli* HB101 (corresponding to Example 9.1.2c). Transformed cells were selected on nutrient agar with tetracycline (25 micrograms/microliter).

9.3 Conversion of pL011 in pRK2013 containing *E. coli* HB101 pRK2013 containing *E. coli* HB101 was selected as a host for pL011. A mobilization in other gram-negative bacteria, such as, *Pseudomonas putida* JD7 with pWWO is possible by the functions coded on pRK2013. Isolated pL011-DNA was transformed into pRK2013 containing *E. coli* HB101, as described in Example 9.1.2a. The selection took place on nutrient agar with tetracycline

9.4 Conjugation of pRK2013 pL011 containing E. coli HB101 with pWWO containing Pseudomonas putida JD7

2 ml was centrifuged off from overnight cultures of both conjugation partners, washed several times in 0.9 percent NaCl (saline), taken up in 100 microliters of saline and mixed on nutrient agar plates. The plates were incubated for conjugation for 6 hours at 30° C. The resulting bacteria lawn was resuspended in 1 ml of saline and plated out in suitable dilutions of nutrient agar with tetracycline (50 micrograms/microliter). With the resulting transconjugants, some pL011 should have been taken up in the TOL plasmid because of homologous recombination.

9.5 Marker exchange between pL011 and pWWO

To remove xylB by homologous recombination from TOL plasmid pWWO in Pseudomonas putida JD7, approximately over 100 generations of the above-obtained E. coli transconjugants were cultured without selection pressure by tetracycline. In this case, the exclusion (removal) of vector pBR322 and intact xylB gene was desired.

To increase the number of tetracycline-sensitive xylB mutants, a selection from integrated vector pBR322 was then performed:

Cells were taken up in 25 ml of complex medium nutrient yeast broth (Oxoid, Wesel, FRG) of tetracycline (50 micrograms/microliter) and incubated up to an $OD_{650}$ of about of 3.0 at 30° C. Then, 500 micrograms/microliter of cycloserine C and 100 micrograms/microliter of piperacillin were added. After incubation for several hours at 30° C., an almost complete lysis of the cells took place. Surviving cells were centrifuged off, washed several times in saline and plated out in suitable dilutions on nutrient agar. Up to 85 percent of the resulting colonies were sensitive to tetracycline.

9.6 Test of the colony for the presence of an xylB deletion

9.6.1 Detection of the deletion with Southern-blot hybridization pWWO'-DNA of the resulting clones was isolated according to the method of Kado and Liu [J. Bacteriol., 145, (1981), pages 1365 to 1373]. For this purpose, 1 ml of overnight culture was centrifuged of and resuspended in 40 mmol of tris-acetate buffer, 2 mmol of EDTA, pH 7.9. The cells were lysed by adding 200 microliters of 3 percent SDS, pH 12.6, incubated for 1 hour at 65° C. and then extracted several times with phenol chloroform (1:1).

The aqueous DNA solution was freed from phenol by repeated washing with diethyl ether and mixed with 1/10 volumes of 3 mol of sodium acetate, pH 4.8. Then, the DNA was precipitated with ethanol and taken up after drying in 100 microliters of water.

About 40 microliters of this DNA sample was cut with 100 units of EcoRI and 5 units of HpaI in a digestive buffer (50 mmol of TRIS, 10 mmol of $MgCl_2$, 100 mmol of NaCl and 1 mmol of DTT, pH 7.5) and subjected to an agarose gel electrophoresis. The DNA transferred to nitrocellulose membranes was hybridized from 500 ng of a pL011 sample labeled $^{32}P$-ATP. The 1.4 kb xylB deletion was directly recognizable after autoradiography.

EXAMPLE 10

Production of the hydroxymethylated heterocycles

E. coli K12* with pL04 (DSM no. 6153) was cultured overnight at 30° C. in nutrient yeast broth (Oxoid, Wesel, FRG) by adding the corresponding antibiotic agent listed in Table 1 corresponding to the method in Example 1.4 for stabilizing the plasmids. Then, an aliquot was transferred in a fresh medium and incubated for another 2 hours at 30° C., before the xylene monooxygenase genes corresponding to the expression system (Table 1) were induced. This took place by adding 1 mmol of IPTG for induction of the expression by the tac-promoter. The induction phase was between 2 and 4 hours in each case. The bacterial suspension was centrifuged and the cellular pellet was then resuspended in fresh medium without adding antibiotics so that an $OD_{650}$ of 10 occurred. This suspension was then mixed with 0.1 percent (v/v for liquid substrates, w/v for solid substrates) of the heterocycles to be oxidized and further incubated at 30.C. After specific periods, the bacterial suspension was examined for product formation.

EXAMPLE 11

Pseudomonas putida JD7 with pL05 was cultured according to Example 10. Because of deficient repressor gene lacIg, an induction with IPTG was able to be dispensed with. The strain was used corresponding to Example 10 for reaction of heterocycles.

EXAMPLE 12

According to Example 10, E. coli K12* with pGSH2836 (DSM no. 6154) was used for the reaction. The induction took place by deactivation of repressor gene cI857 by temperature effect for 2 hours at 42° C.

EXAMPLES 13 AND 14

According to Example 10, the production strains produced in Examples 2 to 8 were used for the reaction.

EXAMPLES 15 TO 20

The results of the conversion rates of the various heterocycles with the production strain of Example 12 are compiled in Table 3.

TABLE 1

| Expression vectors (without) xylMA | Described in | Hybrid-plasmids with xylMA | Characterized by | Size in kb |
| --- | --- | --- | --- | --- |
| pLV85 | J. Bacteriol., 169, (1987), pp. 4457–4462 | pGSH2836 | ampicillin-resistant promoter lambda PL | 5.25 |
| pME285 | Gene, 36, (1985), pp. 27–36 | pLO2 | kanamycin-sensitive mercuric salt resistant mob+ | 12.95 |
| pKT240 | Gene, 26, (1983), pp. 273–282 | pLO3 | kanamycin-sensitive ampicillin-resistant mob+ | 15.25 |
| pMMB67EH | Gene, 48, (1986) pp. 119–131 | pLO4 | ampicillin-resistant promoter $P_{tac}$lacIq+ | 11.15 |
| pMMB67EH* | — | pLO5 | ampicillin-resistant promoter $P_{tac}$lacIq− kanamycin-resistant | 13.5 |

TABLE 2

Production strains for Hydroxylation of Methyl Groups

| Ex. | Production strains | Containing hybrid plasmid or mutated plamid (PWWO') | DSM deposit number | Yield in % in the case of reaction of 2-chloro-5-methyl-pyrimidine as substrate in a concentration of 0.1% (v/v) |
|---|---|---|---|---|
| 2 | E. coli K12* | pGSH2836 | 6154 | 80 |
| 3 | E. coli K12* | pLO4 | 6153 | 80 |
| 4 | E. coli K12* | pLO3 | — | 80 |
| 5 | E. coli K12* | pLO5 | — | 80 |
| 6 | Pseudomonas aeruginosa PAO25 | pLO5 | — | 10 |
| 7 | Pseudomonas putida JD7 | pLO5 | 6152 | 5 |
| 8 | Pseudomonas putida | pLO5 | — | 5 |

TABLE 3

Microbiological oxidation of methylated aromatic heterocycles with microorganism strain: E. coli K12* containing expression vector pGSH2836

| Ex. | Substrate | Concentration of the substr. in the culture medium | Reaction time in hours | End Product | Yield in % |
|---|---|---|---|---|---|
| 15 | 2-chloro-5-methyl-pyridine | 0.1% (v/v) | 16 | 2-chloro-5-hydroxymethyl-pyridine | 80 |
| 16 | 2,5-dimethyl-pyrazine | 0.1% (v/v) | 16 | 2-hydroxymethyl-5-methyl-pyrazine | 50 |
| 17 | 2,6-dimethyl-pyrimidine | 0.1% (w/v) | 16 | 2-hydroxymethyl-4-methylpyrimidine | 10 |
| 18 | 3,5-dimethyl-pyrazone | 0.1% (w/v) | 16 | 3-hydroxymethyl-6-methylpyrazole | 10 |
| 19 | 4-methylthiazole | 0.1% (v/v) | 16 | 4-hydroxymethyl-thiazole | 10 |
| 20 | 2,5-dimethyl-thiophene | 0.1% (v/v) | 16 | 2-hydroxymethyl-5-methylthiophene | 10 |

What is claimed is:

1. Microbiological process comprising hydroxylating the methyl group or methyl groups in a methylated 5- or 6-atom aromatic heterocycle, the reaction being performed with microorganisms which:
   (a) contain the genes of a Pseudomonas TOL plasmid, which form an active xylene monooxygenase, and
   (b) form no effective chromosomally or plasmid-coded alcohol dehydrogenase, and, thus, are capable of hydroxylating the methyl group or methyl groups of the methylates 5- or 6-atom aromatic heterocycle to the corresponding hydroxymethyl derivative, the heterocycle being used as a substrate for the reaction and having no substituents on the carbon atom adjacent to the methyl group to be hydroxylated, and the hydroxymethyl derivative not being further catabolized.

2. Process according to claim 1 wherein the reaction is performed with a microorganism in which the genes come from a Pseudomonas TOL plasmid which form an effective xylene monooxygenase and are characterized by the restriction map in the FIGURE.

3. Process according to claim 2 wherein the reaction is performed with a microorganism which belongs to a genus selected from the group consisting of Pseudomonas, Acinetobacter, Rhizobium, Agrobacterium and Escherichia.

4. Process according to claim 3 wherein the reaction is performed with the microorganism of species Escherichia coli K12*, transformed with hybrid plasmid pGSH2836 (DSM no. 6154), or a descendant thereof or a mutant thereof.

5. Process according to claim 3 wherein the reaction is performed with the microorganism of species Escherichia coli K12* transformed with hybrid plasmid pLO4 (DSM No. 6153), or a descendant thereof or a mutant thereof.

6. Process according to claim 3 wherein the reaction is performed with the microorganism of species Pseudomonas putida JD7 transformed with hybrid plasmid pLO5 (DSM no. 6152), or a descendant thereof or a mutant thereof.

7. Process according to claim 6 wherein the reaction is performed with a methylated 5- or 6-atom heterocycle, which contains one or more heteroatoms selected from the group consisting of oxygen, nitrogen and sulfur.

8. Process according to claim 7 wherein the reaction is performed either with single or continuous addition of substrate so that the substrate concentration in the culture medium does not exceed 20 percent (w/v) or (v/v).

9. Process according to claim 8 wherein the reaction is performed at a pH of 4 to 11 and at a temperature of 15° to 50° C.

10. Process according to claim 1 wherein the reaction is performed with a microorganism, which contains a natural TOL plasmid, in which the gene, which is the code for an effective alcohol dehydrogenase, is removed or deactivated.

11. Process according to claim 1 wherein the reaction is performed with a microorganism which belongs to a genus selected from the group consisting of Pseudomonas, Acinetobacter, Rhizobium, Agrobacterium and Escherichia.

12. Process according to claim 1 wherein the reaction is performed with the microorganism of species Escherichia coli K12*, transformed with hybrid plasmid pGSH2836 (DSM no. 6154), or a descendant thereof or a mutant thereof.

13. Process according to claim 1 wherein the reaction is performed with the microorganism of species Escherichia coli K12* transformed with hybrid plasmid pLO4 (DSM no. 6153) or a descendant thereof or a mutant thereof.

14. Process according to claim 1 wherein the reaction is performed with the microorganism of species *Pseudomonas putida* JD7 transformed with hybrid plasmid pL05 (DSM no. 6152), or a descendant thereof or a mutant thereof.

15. Process according to claim 1 wherein the reaction is performed with a methylated 5- or 6-atom heterocycle, which contains one or more heteroatoms selected from the group consisting of oxygen, nitrogen and sulfur.

16. Process according to claim 1 wherein the reaction is performed with either single or continuous addition of substrate so that the substrate concentration in the culture medium does not exceed 20 percent (w/v) or (v/v).

17. Process according to claim 1 wherein the reaction is performed at a pH of 4 to 11 and at a temperature of 15° to 50° C.

* * * * *